United States Patent [19]
Mathur

[11] Patent Number: 5,489,523
[45] Date of Patent: Feb. 6, 1996

[54] **EXONUCLEASE-DEFICIENT THERMOSTABLE *PYROCOCCUS FURIOSUS* DNA POLYMERASE I**

[75] Inventor: Eric J. Mathur, Solana Beach, Calif.

[73] Assignee: Stratagene, La Jolla, Calif.

[21] Appl. No.: 966,278

[22] Filed: Oct. 26, 1992

Related U.S. Application Data

[63] Continuation-in-part of Ser. No. 803,627, Dec. 2, 1991, which is a continuation-in-part of Ser. No. 776,552, Oct. 18, 1991, abandoned, which is a continuation-in-part of Ser. No. 657,073, Feb. 19, 1991, abandoned, which is a continuation-in-part of Ser. No. 620,568, Dec. 3, 1990, abandoned.

[51] Int. Cl.$^6$ .............. C12N 9/12; C12N 15/54; C12N 15/63; C12N 15/70
[52] U.S. Cl. .......... 435/194; 435/69.1; 435/71.2; 435/320.1; 435/172.3; 435/252.3; 435/252.33; 935/10; 935/14; 935/29; 935/56; 935/73; 536/23.2
[58] Field of Search ............ 435/194, 69.1, 435/71.2, 320.1, 172.3, 252.3; 935/10, 14, 29, 56, 73; 536/23.2

[56] References Cited

U.S. PATENT DOCUMENTS

| | | | |
|---|---|---|---|
| 4,889,818 | 12/1989 | Gelfand et al. | 435/194 |
| 4,994,372 | 2/1991 | Tabor et al. | 435/6 |
| 5,352,778 | 10/1994 | Comb et al. | 536/23.2 |

OTHER PUBLICATIONS

E. J. Mathur et. al. J. Cell. Biochem. 16B:29 (Jan. 1992).
K. S. Lundberg et al. FASEB J. 5(6) A1549 (Mar. 1991).
E. J. Mathur et al. Nuc. Acids Res. 19(24)69S2 (Dec. 1991).
P. Forterre Nuc. Acids. Res. 20(7) 1811 (Apr. 1992).
M. P. Deutscher, "Guide to Protein Purification" Meth. in Enzymol. 182:738–751 (1990.
S. L. Berger et al. "Guide to Molecular Cloning Techniques" Meth. in Enzymol. 152:393–399, 415–423, 432–449, 661–704 (1987).
F. O. Bryant. et al. "Characterization of Hydrogenase from the Hyperthermophilic Archaebacterium *Pyroccus furiosus*" J. Biol Chem. 264(9) 5070–5079 (Mar. 1989).
F. C. Laywer et al. "Isolation, Characterization and Expression . . . " J. Biol Chem. 264(11) 6427–6437 (Apr. 1989).
K. S. Lundberg et al. "High Fidelity Amplification Using . . . " Gene 108:1–6 (1991).
A. Bernat et al. "A Conserved 3'→5' Exonuclease Active . . . " Cell 59: 219–228 (1989).
J. S. Lee "Alternative Dideoxy Sequencing of Double–Stranded . . . " DNA Cell. Biol. 10(1) 67–73 (1991).
L. Baneo et al. "Evidence Favoring the Hypothesis of . . . " Gene 112(1) 139–144 (Mar. 1992).

Primary Examiner—Robert A. Wax
Assistant Examiner—Rebecca Prouty
Attorney, Agent, or Firm—Albert P. Halluin; Pennie & Edmonds

[57] ABSTRACT

A recombinant thermostable *Pyrococcus furiosus* DNA polymerase is described that is deficient in 3'–5' exonuclease activity that is useful in DNA cycle sequencing reactions.

9 Claims, 2 Drawing Sheets

EXONUCLEASE-DEFICIENT THERMOSTABLE *PYROCOCCUS FURIOSUS* DNA POLYMERASE I

CROSS REFERENCE

This application is a continuation-in-part of U.S. patent application Ser. No. 07/803,627 filed Dec. 2, 1991, which is a continuation-in-part application of application Ser. No. 7/776,552, filed Oct. 18, 1991 now abandoned, which is a continuation-in-part of application Ser. No. 07/657,073, filed Feb. 19, 1991 now abandoned, which is a continuation-in-part of application Ser. No. 07/620,568, filed Dec. 3, 1990 now abandoned.

TECHNICAL FIELD

The present invention relates to a 3' to 5' exonuclease deficient thermostable enzyme having DNA polymerase I activity useful in nucleic acid synthesis by primer extension reactions, particularly DNA cycle-sequencing reactions.

BACKGROUND

The archaebacteria are a recently discovered group of microorganisms that grow optimally at temperatures above 80° C. Some 20 species of these extremely thermophilic bacteria-like organisms have been isolated, mainly from shallow submarine and deep sea geothermal environments. Most of the archaebacteria are strict anaerobes and depend on the reduction of elemental sulfur for growth.

The archaebacteria include a group of "hyperthermophiles" that grow optimally around 100° C. These are presently represented by three distinct genera, Pyrodictium, Pyrococcus, and Pyrobaculum. *Phyodictium brockii* ($T_{opt}$ 105° C.) is an obligate autotroph which obtains energy be reducing $S^0$ to $H_2S$ with $H_2$, while *Pyrobaculum islandicum* ($T_{opt}$ 100° C.) is a facultative heterotroph that uses either organic substrates or $H_2$ to reduce $S^0$. In contrast, *Pyrococcus furiosus* ($T_{opt}$ 100° C.) grows by a fermentative-type metabolism rather than by $S^0$ respiration. It is a strict heterotroph that utilizes both simple and complex carbohydrates where only $H_2$ and $CO_2$ are the detectable products. The organism reduces elemental sulfur to $H_2S$ apparently as a form of detoxification since $H_2$ inhibits growth.

The discovery of microorganisms growing optimally around 100° C. has generated considerable interest in both academic and industrial communities. Both the organisms and their enzymes have the potential to bridge the gap between biochemical catalysis and many industrial chemical conversions. However, knowledge of the metabolism of the hyperthermophilic microorganisms is presently very limited.

The polymerase chain reaction (PCR) is a powerful method for the rapid and exponential amplification of target nucleic acid sequences. PCR has facilitated the development of gene characterization and molecular cloning technologies including the direct sequencing of PCR amplified DNA, the determination of allelic variation, and the detection of infectious and genetic disease disorders. PCR is performed by repeated cycles of heat denaturation of a DNA template containing the target sequence, annealing of opposing primers to the complementary DNA strands, and extension of the annealed primers with a DNA polymerase. Multiple PCR cycles result in the exponential amplification of the nucleotide sequence delineated by the flanking amplification primers.

An important modification of the original PCR technique was the substitution of *Thermus aquaticus* (Taq) DNA polymerase in place of the Klenow fragment of *E. coli* DNA pol I (Saiki, et al. *Science*, 230:1350–1354 (1988)). The incorporation of a thermostable DNA polymerase into the PCR protocol obviates the need for repeated enzyme additions and permits elevated annealing and primer extension temperatures which enhance the specificity of primer:template associations. Thermostability in a polymerase thus serves to increase the specificity and simplicity of PCR.

Recently, a thermostable DNA polymerase was isolated from *P. furiosus* (Pfu), referred to as Pfu DNA polymerase. Lundberg et al., *Gene*, 108:1–6 (1991). Pfu DNA polymerase exhibits a higher temperature optimum than Taq DNA polymerase, thereby making it an important thermostable DNA polymerase.

Linear amplification sequencing, also known as cycle sequencing, is rapidly becoming the method of choice for sequencing difficult templates. Murray, *Nuc. Acids Res.*, 17:8889 (1989); and Craxton, *Methods: A Companion to Methods in Enzymology*, 3:20–26 (1991). PCR products, direct colonies and phage plaques can be sequenced using the cycle sequencing procedure. to date, Taq DNA polymerase has been almost exclusively used for cycle sequencing reactions.

However, there are several inherent disadvantages to using Taq DNA polymerase in cycle sequencing. Taq DNA polymerase incorporates thiolated nucleotides such as $^{35}S$-dATP very inefficiently because the enzyme discriminates highly against ddNTP analogs. $^{35}S$-dATP is the most widely used label in DNA sequencing today, at least because it is considerably safer to use than the other common labels such as $^{32}P$- or $^{33}P$-labelled dNTP's. In addition, Taq DNA polymerase loses considerable activity when used in cycling reactions at temperatures required for template denaturation, such as cycle sequencing reactions.

DNA polymerase from *Thermococcus litoralis* has recently been described ("Vent" polymerase) which has significant thermostability. However, cycle sequencing with Vent DNA polymerase exhibits an additional problem referred to as "stuttering" which arises from the editing function present in the 3' to 5' exonuclease activity present in the enzyme. Stuttering leads to excessive bands in the sequencing reaction and produces unreadable sequencing gels. The thermolabile DNA polymerase from *E. coli* has been characterized toy contain protein domains responsible for the 3' to 5' exonuclease activity as described by Morrison et al., *Proc. Natl. Acad. Sci. USA*, 88:9473–9477 (1991). However, similar domains have not been identified in a thermostable DNA polymerase. Thus there is a need for thermostable DNA polymerases other than Vent DNa polymerase with less 3' to 5' HP LaserJet Series IIHPLASEI-I.PRS Vent and CircumVent are available from New England Biolabs (NEB) and have been described by Sears et al., *Biotechniques*, 13:626–633 (1992). However, both enzymes exhibit thermo-instability upon prolonged exposure to temperatures of about 95° C. that are often used in cycle sequencing.

There continues to be a need for a highly thermostable DNA polymerase useful in cycle sequencing which is deficient in 3'–5' exonuclease activity and which efficiently incorporates thiolated dNTP analogs in DNA polymerization reactions.

SUMMARY OF THE INVENTION

A modified thermostable DNA polymerase has been produced from the DNA polymerase of hyperthermophilic, marine archaebacterium, *Pyrococcus furiosus* (Pfu) that provides a solution to the technical problems posed above. The monomeric enzyme possesses DNA polymerase activity, but is deficient in 3' to 5' exonuclease activity. The polymerase is extremely thermostable through a temperature range of about 0° C. to about 104° C., and exhibits DNA polymerase activity in temperatures of from about 40°to 90° C., with an activity optimum at about 75° C. The purified enzyme functions effectively in the polymerase chain reaction (PCR). The 3' to 5' exonuclease dependent proofreading activity of the wild type Pfu DNA polymerase is made deficient by selective substitution of amino acid residues required for the 3' to 5' exonuclease activity without inhibiting the DNA polymerase activity. The 3' to 5' exonuclease-deficient modified enzyme is referred to as an exo⁻Pfu DNA polymerase to connote the reduced exonuclease activity.

Exo⁻Pfu DNA polymerase remains greater that 95% active after one hour incubation at 95° C. In contrast, Vent polymerase and CircumVent DNA polymerase [New England Biolabs (NEB) Beverly, Mass.], and Taq DNA polymerase, lose greater than 30% of their polymerase activity after one hour incubation at 95° C. Exo⁻Pfu DNA polymerase is thus unexpectedly superior to Taq, Vent and CircumVent DNA polymerases in amplification protocols such as cycle sequencing.

The apparent molecular weight of the native protein is about 90,000–93,000 daltons as determined by SDS-PAGE under denaturing conditions. Preferred exo⁻Pfu DNA polymerase proteins have the same apparent molecular weight as the native enzyme.

Thus, the present invention contemplates a recombinant thermostable *Pyrococcus furiosus* DNA polymerase I deficient in 3' to 5' exonuclease activity. Preferably, the polymerase has an amino acid residue sequence represented by the formula shown in SEQ ID NO 1 from residue 1 to residue 775, with the exception of an amino acid residue substitution selected from the group consisting of (1) $Ala^{141}/Ala^{143}$, (2) $Ala^{214}/Ala^{215}$, and (3) $Ala^{311}/Ala^{315}$. A particularly preferred polymerase retains at least 95% of its DNA polymerase activity after exposure to 95° C. for 1 hour. Preferably, a polymerase of this invention has less than 50 units of specific 3' to 5' exonuclease activity per milligram of protein. Stated differently, a polymerase of this invention preferably has a ratio of specific activity of DNA polymerase activity to 3'–5' exonuclease activity of at least 1000.

Also contemplated is a plasmid containing a gene coding for an exo⁻Pfu DNA polymerase of this invention, a procaryotic cell transformed with the plasmid of this invention, and a bacteriophage containing a gene coding for an exo⁻Pfu DNA polymerase of this invention.

BRIEF DESCRIPTION OF THE DRAWINGS

In the drawings forming a portion of this disclosure.

DETAILED DESCRIPTION OF THE INVENTION

A. Definitions

Figure 1:
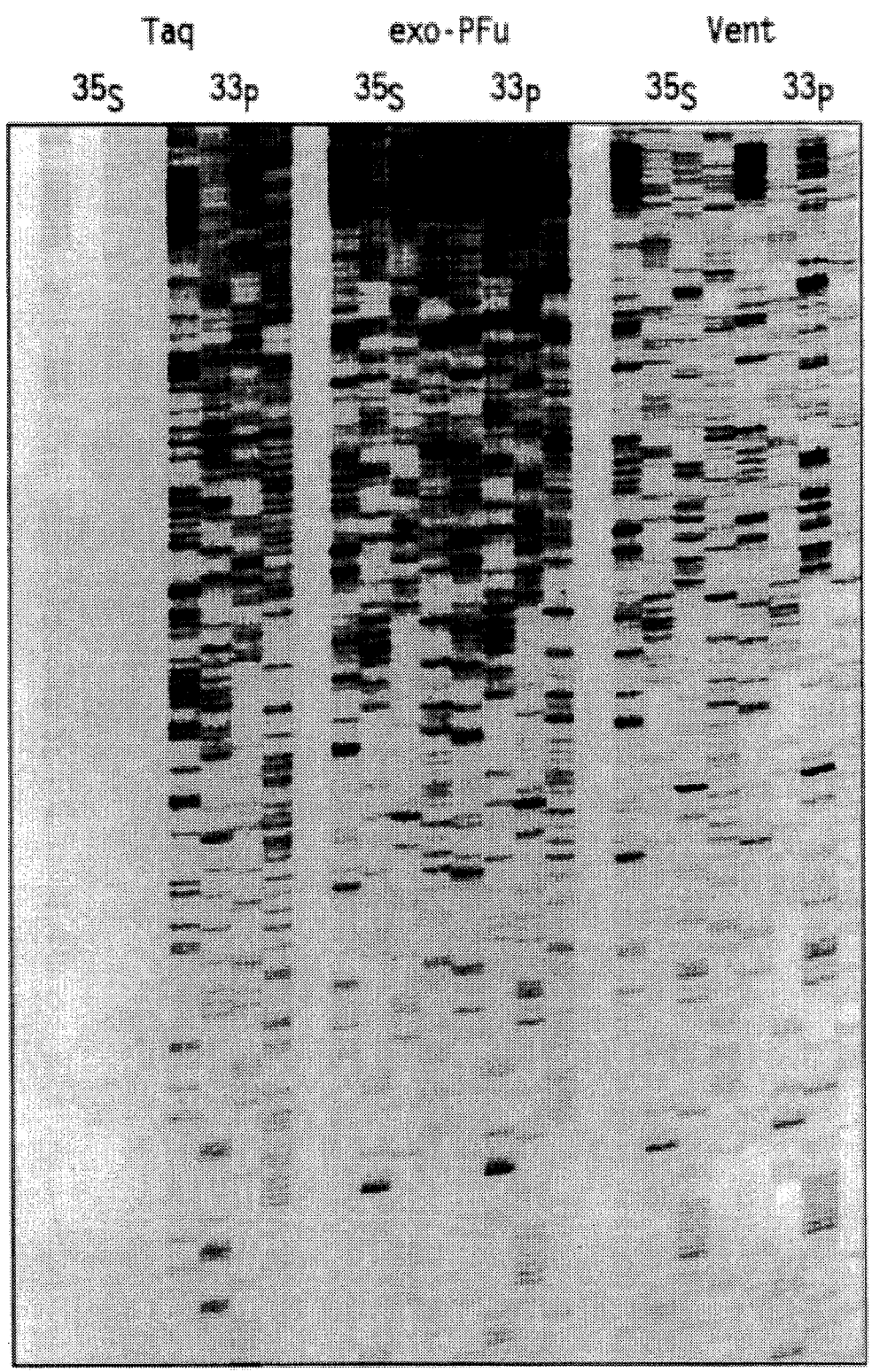
FIG. 1 illustrates the sequencing ladder prepared by cycle-sequencing using various DNA polymerases as described in Example 6. Six percent (6%) acrylamide/urea sequencing gels were run after cycle sequencing analysis of double-stranded pBluescript plasmid DNA using either $^{35}S$-dATP (A) or $^{33}P$-dTTP (B) in a cycle sequencing reaction with either Taq DNA polymerase (Taq), Vent DNA polymerase (Vent) or exo⁻Pfu DNA polymerase (exo⁻Pfu).

As used herein, "cell", "cell line", and "cell culture" can be used interchangeably and all such designations include progeny. Thus, the words "transformants" or "transformed cells" includes the primary subject cell and cultures derived therefrom without regard for the number of transfers. It is also understood that all progeny may not be precisely identical in DNA content, due to deliberate or inadvertent mutations. Mutant progeny that have the same functionality as screened for in the originally transformed cell are included.

The term "control sequences" refers to DNA sequences necessary for the expression of an operably linked coding sequence in a particular host organism. The control sequences that are suitable for procaryotes, for example, include a promoter, optionally an operator sequence, a ribosome binding site, and the like. Eucaryotic cells are known to utilize promoters, polyadenylation signals, and enhancers.

The term "expression system" refers to DNA sequences containing a desired coding sequence and control sequences in operable linkage, so that hosts transformed with these sequences are capable of producing the encoded proteins. In order to effect transformation, the expression system may be included on a vector; however, the relevant DNA may then also be integrated into the host chromosome.

The term "gene" as used herein refers to a DNA sequence that encodes a polypeptide.

"Operably linked" refers to juxtaposition such that the normal function of the components can be performed. Thus, a coding sequence "operably linked" to control sequences refers to a configuration wherein the coding sequences can be expressed under the direction of the control sequences.

The term "oligonucleotide" as used herein is defined as a molecule comprised of two or more deoxyribonucleotides and/or ribonucleotides, preferably more than three. Its exact size will depend on many factors, which in turn depend on the ultimate function or use of the oligonucleotide. The oligonucleotide may be derived synthetically or by cloning.

The term "primer" as used herein refers to an oligonucleotide, whether occurring naturally or produced synthetically, which is capable of acting as a point of initiation of nucleic acid synthesis when placed under conditions in which synthesis of a primer extension product which is complementary to a nucleic acid strand is induced, i.e., in the presence of four different nucleotide triphosphates and thermostable enzyme in an appropriate buffer ("buffer" includes pH, ionic strength, cofactors, etc.) and at a suitable temperature. For exo⁻Pfu DNA polymerase, the buffer herein preferably contains 1.5–2 mM of a magnesium salt, preferably $MgCl_2$, 150–200 μM of each nucleotide, and 1 uM of each primer, along with preferably 50 mM KCl, 20 mM Tris buffer, pH 8–8.4, and 100 μg/ml gelatin.

The primer is preferably single-stranded for maximum efficiency in amplification, but may alternatively be double-stranded. If double-stranded, the primer is first treated to separate its strands before being used to prepare extension products. Preferably, the primer is an oligodeoxyribonucleotide. The primer must be sufficiently long to prime the synthesis of extension products in the presence of the thermostable enzyme. The exact lengths of the primers will depend on many factors, including temperature, source of primer and use of the method. For example, depending on the complexity of the target sequence, the oligonucleotide primer typically contains 15–25 nucleotides, although it may contain more or few nucleotides. Short primer molecules generally require colder temperatures to form sufficiently stable hybrid complexes with template.

The primers herein are selected to be "substantially" complementary to the different strands of each specific sequence to be amplified. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to be amplified to hybridize therewith and thereby form a template for synthesis of the extension product of the other primer. However, for detection purposes, particularly using labeled sequence-specific probes, the primers typically have exact complementarity to obtain the best results.

As used herein, the term "thermostable enzyme" refers to an enzyme which is stable to heat and is heat resistant and catalyzes (facilitates) combination of the nucleotides in the proper manner to form the primer extension products that are complementary to each nucleic acid strand. Generally, the synthesis will be initiated at the 3' end of each primer and will proceed in the 5' direction along the template strand, until synthesis terminates, producing molecules of different lengths.

Amino Acid Residue: The amino acid residues described herein are preferred to be in the "L" isomeric form. However, residues in the "D" isomeric form can be substituted for any L-amino acid residue, as long as the desired functional property is retained by the polypeptide. NH2 refers to the free amino group present at the amino- or carboxy-terminus of a polypeptide. COOH refers to the free carboxy group present at the carboxy terminus of a polypeptide. The amino-terminal NH$_2$ group and carboxy-terminal COOH group of free polypeptides are typically not set forth in a formula. A hyphen at the amino- or carboxy-terminus of a sequence indicates the presence of a further sequence of amino acid residues or a respective NH$_2$ or COOH terminal group. In keeping with standard polypeptide nomenclature, *J. Biol. Chem.*, 243:3552–59 (1969) and adopted at 37 CFR §1.822(b)(2), abbreviations for amino acid residues are shown in the following Table of Correspondence:

| TABLE OF CORRESPONDENCE | | |
|---|---|---|
| SYMBOL | | |
| 1-Letter | 3-Letter | AMINO ACID |
| Y | Tyr | tyrosine |
| G | Gly | glycine |
| F | Phe | phenylalanine |
| M | Met | methionine |

| TABLE OF CORRESPONDENCE | | |
|---|---|---|
| SYMBOL | | |
| 1-Letter | 3-Letter | AMINO ACID |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino acid residue sequences are represented herein by formulae whose left and right orientation is in the conventional direction of amino-terminus to carboxy-terminus.

Nucleotide: a monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. When the nucleoside contains a phosphate group bonded to the 3' or 5' position of the pentose it is referred to as a nucleotide. A sequence of operatively linked nucleotides is typically referred to herein as a "base sequence" or "nucleotide sequence", and is represented herein by a formula whose left to right orientation is in the conventional direction of 5'-terminus to 3'-terminus.

Base Pair (bp): A partnership of adenine (A) with thymine (T), or of cytosine (C) with guanine (G) in a double stranded DNA molecule.

B. Exonuclease-Deficient Pfu DNA Polymerase I

Exo$^-$Pfu DNA polymerase, the thermostable DNA polymerase of the present invention, is substantially deficient in 3' to 5' exonuclease activity. By substantially deficient is meant that there is less than 100 units (U) per milligram (mg) of purified enzyme, preferably less than 50 U/mg, and more preferably less than 10 U/mg. A purified enzyme is at least 98% homogeneous when resolved on SDS gel molecular weight electrophoresis.

Assays for 3' to 5' exonuclease activity are well known in the art. A preferred assay is described in Example 4.

An exo$^-$Pfu DNA polymerase preferably has DNA polymerase activity, expressed as specific activity, of at least about 10,000 units (10 KU) per mg of polymerase protein, and preferably at least about 15 KU/mg, and more preferably at least 25 KU/mg.

Insofar as a utility of the present resides in the exonuclease deficiency, a subject polymerase preferably has a ratio of specific activities of DNA polymerase to 3'–5' exonuclease activity of at least 50 (50 U polymerase per U of exonuclease), preferably at least about 100–500, and more preferable at least about 1000 to 4000.

For the enzyme to be thermostable according to the present invention, it must satisfy a single criterion to be effective for the amplification reaction, i.e., the enzyme must not become irreversibly denatured (inactivated) when subjected to the elevated temperatures for the time necessary to effect denaturation of double-stranded nucleic acids. Irreversible denaturation for purposes herein refers to permanent and complete loss of enzymatic activity. The heating conditions necessary for denaturation will depend, e.g., on the buffer salt concentration and the length and nucleotide composition of the nucleic acids being denatured, but typically range from about 90° to about 96° C. for a time depending mainly on the temperature and the nucleic acid length, typically about 0.5 to four minutes. Higher temperatures may be tolerated as the buffer salt concentration and/or GC composition of the nucleic acid is increased. Preferably, the enzyme will not become irreversibly denatured at about 90°–100° C. Stated differently, an enzyme of this invention loses less that 25 percent of its DNA polymerase activity after exposure to 95° C. for 1 hour (hr), preferably less than 10%, and still more preferably less than 5% of its activity.

By "recombinant Pfu DNA polymerase" is meant that the subject enzyme is a recombinant protein derived from the DNA polymerase of *Pyrococcus furiosus*. Preferably, the subject polymerase has an amino acid residue sequence that substantially corresponds to the amino acid residue sequence of the native Pfu enzyme, except for certain specified substitutions producing the desired activity. By "substantially corresponds" means that the sequence is at least 80% homologous, preferably at least 90% homologous, and more preferably is at least 98% homologous to the native enzyme.

A preferred exo⁻Pfu DNA polymerase has the amino acid residue sequence of the native Pfu DNA polymerase, with the exception of the substitution of one or more amino acid residues as to reduce the 3'–5' exonuclease activity and thereby render the polymerase substantially deficient in the exonuclease activity. Any of a number of amino acid substitutions in the subject polymerase are contemplated, so long as the requisite activity is produced.

Thus, the amino acid residue sequence of a preferred exo⁻Pfu DNA polymerase is shown in SEQ ID NO 1 from residue 1 to 775, except that amino acid substitutions are present which confer exonuclease deficiency as described herein. The amino acid residue sequence of a subject exo⁻ Pfu DNA polymerase can be determined by any suitable method, such as by automated Edman degradation, and the like.

Preferred substitutions are present in selected amino acid residues of the native Pfu DNA polymerase amino acid residue sequence in exonuclease-dependent domains of the enzyme located within residues 134–151 (site I), residues 204–219 (site II) or residues 306–319 (site III) of the amino acid residue sequence shown in SEQ ID NO 1. Particularly preferred substitutions are in one or more of the residues selected from the group consisting of $Asp^{141}$, $Glu^{143}$, $Phe^{214}$, $Asp^{215}$, $Tyr^{311}$ and $Asp^{315}$. Particularly preferred are substitutions to a pair of residues selected from the group consisting of (1) $Asp^{141}$ and $Glu^{143}$; (2) $Phe^{214}$ and $Asp^{215}$; and $Tyr^{311}$ and $Asp^{315}$.

Any amino acid residue may be the residue substituted in place of the native residue, so long as the requisite activity is produced. However, substitutions with non-charged residues such as leucine, valine, glycine, alanine, and the like are preferred, although alanine is most preferred. Particularly preferred substitutions are those in which the resulting subject polymerase has a sequence shown in SEQ ID NO 1 with the exception that the polymerase has a substitution selected from the group consisting of (1) $Ala^{141}/Ala^{143}$, (2) $Ala^{214}/Ala^{215}$, and (3) $Ala^{311}/Ala^{315}$. Exemplary are the exo⁻Pfu DNA polymerase proteins expressed by the vectors pJCF72-1, pJCF72-2 and pJCF72-3.

The molecular weight of the dialyzed product may be determined by any technique, for example, by sodium dodecylsulfate-polyacrylamide gel electrophoresis (SDS-PAGE) using protein molecular weight markers. Recombinant exo⁻Pfu DNA polymerase purified by the above method has a relative molecular weight, determined by SDS-PAGE under denaturing conditions, of about 90,000–93,000 daltons.

In preferred embodiments, exo⁻Pfu DNA polymerase is used in combination with a thermostable buffering agent such as TAPS (N-tris[Hydroxymethyl]methyl-3-aminopropanesulfonic acid; ([2-Hydroxy- 1, 1-bis(hydroxy-methyl)-ethyl]amino-1-propanesulfonic acid), available from Sigma, St. Louis, Mo. (Catalog P7905).

Thus, the invention also contemplates compositions containing an enzymatically active amount of an exo⁻Pfu DNA polymerase in a compatible buffer.

C. Production of Recombinant Exo⁻Pfu DNA Polymerase

Exo⁻Pfu DNA polymerase is typically produced by recombinant DNA (rDNA) techniques, from a gene encoding the modified enzyme. Thus, the present invention also contemplates a DNA segment consisting essentially of a sequence of nucleotide bases encoding a exo⁻Pfu DNA polymerase of this invention. An exemplary DNA sequence, obtained from the native gene and containing certain preselected nucleotide substitutions, is shown in SEQ ID NO 2 from nucleotide base 224 to base 2548, which spans the coding portion of SEQ ID NO 2, except for the nucleotide substitutions described herein to render the native protein 3' to 5' exonuclease deficient. Those substitutions have been described earlier.

The isolated gene can be operably linked to an expression system to form an rDNA capable of expressing, in a compatible host, exo⁻Pfu DNA polymerase.

Of course, modifications to the primary structure itself by deletion, addition, or alteration of the amino acids incorporated into the protein sequence during translation can be made without destroying the activity of the protein. Such substitutions or other alterations result in proteins having an amino acid sequence encoded by DNA falling within the contemplated scope of the present invention.

From the clone pF72 described in the Examples, the nucleotide sequence of a preferred gene encoding native recombinant Pfu DNA polymerase I was described and is shown in SEQ ID NO 2, and can be utilized for the production of recombinant exo⁻Pfu DNA polymerase.

In general terms, the production of a recombinant form of exo⁻Pfu DNA polymerase typically involves the following:

First, a DNA is obtained that encodes the mature native enzyme or a fusion protein of the native Pfu DNA polymerase either to an additional sequence that does not destroy its activity, or to an additional sequence cleavable under controlled conditions (such as treatment with peptidase) to give an active protein. If the sequence is uninterrupted by introns it is suitable for expression in any host. This sequence should be in an excisable and recoverable form.

Thereafter, the nucleotides within the provided gene containing the Pfu DNA polymerase coding sequence are mutated in the region of the gene that encodes that portion of the enzyme which is responsible for the 3' to 5' exonuclease activity of Pfu DNa polymerase. Those sites were described earlier.

Mutation can be accomplished by a variety of methods well known in the art that are not critical to the invention. Mutation methods include, but are not limited to site directed mutation, random mutation, error prone PCR, in vitro mutagenesis using oligonucleotides, and the like. A preferred mutation procedure is described herein the Examples. The resulting mutated gene encodes a recombinant, thermostable exo⁻Pfu DNA polymerase.

The mutated gene is then provided in the form of a DNA segment (excised or recovered coding sequence) that encodes the recombinant, exo⁻Pfu DNA polymerase protein using standard techniques.

The excised or recovered coding sequence is then preferably placed in operable linkage with suitable control sequences in a replicable expression vector. The vector is used to transform a suitable host and the transformed host cultured under favorable conditions to effect the production of the recombinant exo⁻Pfu DNA polymerase by expression of the gene and subsequent protein production in the compatible transformed host.

The expressed exo⁻Pfu DNA polymerase is isolated from the medium or from the cells; recovery and purification of the protein may not be necessary in some instances, where some impurities may be tolerated.

The isolation and purification of exo⁻Pfu DNA polymerase can take place in a variety of ways, although a preferred method is described herein. Typically, the purified protein is dialyzed after purification against a low salt buffer, e.g., 50 mM Tris pH 7.5, 1 mM dithiothreitol, 0.1 mM EDTA, 0.1% Tween 20, and 0.1% non-idet P40 (NP40). Typically, a stabilizing agent, such as glycerol, is added to the preparation to facilitate low temperature storage of the purified, recombinant enzyme.

Each of the foregoing steps can be done in a variety of ways. For example, the desired coding sequences may be obtained from genomic fragments and used directly in appropriate hosts. The constructions for expression vectors operable in a variety of hosts are made using appropriate replicons and control sequences, as set forth below. Suitable restriction sites can, if not normally available, be added to the ends of the coding sequence so as to provide an excisable gene to insert into these vectors.

The control sequences, expression vectors, and transformation methods are dependent on the type of host cell used to express the gene. Generally, procaryotic, yeast, insect or mammalian cells are presently useful as hosts. Procaryotic hosts are in general the most efficient and convenient for the production of recombinant proteins and therefore are preferred for the expression of exo⁻Pfu DNA polymerase.

Procaryotes most frequently are represented by various strains of *E. coli*. However, other microbial strains may also be used, such as bacilli, for example, Bacillus subtillis, various species of Pseudomonas, or other bacterial strains. In such procaryotic systems, plasmid vectors that contain replication sites and control sequences derived from species compatible with the host are used. For example, *E. coli* is typically transformed using derivatives of pBR322, a plasmid derived from an *E. coli* species by Bolivar, et al., *Gene*, (1977) 2:95 and Sutcliffe, *Nuc. Acids Res.*, (1978) 5:2721–28. pBR322 contains genes for ampicillin and tetracycline resistance, and thus provides additional markers that can be either retained or destroyed in constructing the desired vector. Commonly used procaryotic control sequences, which are defined herein to include promoters for transcription initiation, optionally with an operator, along with ribosome binding site sequences, include such commonly used promoters as the B-lactamase (penicillinase) and lactose (lac) promoter systems (Chang, et al., *Nature*, (1977) 198:1056), the tryptophan (trp) promoter system (Goeddel, et al., *Nucleic Acids Res.*, (1980) 8:4057) and the lambda-derived $P_L$ promoter (Shimatake, et al., *Nature*, (1981) 292:128) and N-gene ribosome binding site, which has been made useful as a portable control cassette (as set forth in U.S. Pat. No. 4,711,845), which comprises a first DNA sequence that is the $P_L$ promoter operably linked to a stream of a third DNA sequence having at least one restriction site that permits cleavage with six bp 3' of the $N_{RBS}$ sequence. Also useful is the phosphatase A (phoA) system described by Change, et al. in European Patent Publication No. 196, 864. However, any available promoter system compatible with procaryotes can be used. Typical bacterial plasmids are pUC8, pUC9, pBR322 and pBR329 available from Bio-Rad Laboratories, (Richmond, Calif.) and pPL and pkk233-2, available from Pharmacia (Piscataway, N.J.) or Clone Tech (Palo Alto, Calif.).

In addition to bacteria, eucaryotic microbes, such as yeast, may also be used as hosts. Laboratory strains of *Saccharomyces cerevisiae*, Baker's yeast, are most used, although a number of other strains are commonly available. While vectors employing the 2 micron origin of replication are illustrated (Broach, J. R., *Meth. Enz.*, (1983) 101:307), other plasmid vectors suitable for yeast expression are known (see, for example, Stinchcomb, et al., *Nature*, (1979) 282:39, Tschempe, et al., *Gene*, (1980) 10:157, Clarke, L., et al., *Meth. Enz* (1983) 101:300), Brake et al., *Proc. Natl. Acad. Sci. USA*, (1984) 81:4642–4647, and Halewell et al., *Biotechnology*, (1987) 5:363–366. Control sequences for yeast vectors include promoters for the synthesis of glycolytic enzymes (Hess, et al., *J. Adv. Enzyme Reg.*, (1968) 7:149; Holland, et al., *Biotechnology* (1978) 17:4900).

Preferred *E. coli* host cells include RR1, XL1Blue (Stratagene), and the like, in addition to the equivalent host cell described herein. Preferred expression vectors for use in an *E. coli* host include pBR322, pBluescript described herein and the like equivalent plasmid expression vectors.

It is also, of course, possible to express genes encoding polypeptides in eucaryotic host cell cultures derived from multicellular organisms. See, for example, *Tissue Culture*, Academic Press, Cruz and Patterson, editors (1973). Useful host cell lines include murine myelomas N51, VERO and HeLa cells, and Chinese hamster ovary (CHO) cells available from the ATCC as CCL61, and NIH/3T3 mouse cells available from the ATCC as CRL1658. Expression vectors for such cells ordinarily include promoters and control sequences compatible with mammalian cells such as, for example, the commonly used early and late promoters from Simian Virus 40 (SV 40) (Fiers, et al., *Nature*, (1978) 273:113), or other viral promoters such as those derived from polyoma, Adenovirus 2, bovine papilloma virus, or avian sarcoma viruses, or immunoglobulin promoters and heat shock promoters. A system for expressing DNA in mammalian systems using the BPV as a vector is disclosed in U.S. Pat. No. 4,419,446. A modification of this system is described in U.S. Pat. No. 4,601,978. General aspects of mammalian cell host system transformations have been described in U.S. Pat. No. 4,399,216. It now appears, also, that "enhancer" regions are important in optimizing expression; these are, generally, sequences found upstream of the promoter region. Origins of replication may be obtained, if needed, from viral sources. However, integration into the chromosome is a common mechanism for DNA replication in eucaryotes.

Plant cells are also now available as hosts, and control sequences compatible with plant cells such as the nopaline synthase promoter and polyadenylation signal sequences (Depicker, A., et al., *J. Mol. Appl. Gen.*, (1982) 1:561) are available. See, also, U.S. Pat. No. 4,962,028, U.S. Pat. No. 4,956,282, U.S. Pat. No. 4,886,753 and U.S. Pat. No. 4,801,540.

Recently, in addition, expression systems employing insect cells utilizing the control systems provided by baculovirus vectors have been described (Miller, D. W., et al., in

*Genetic Engineering* (1986) Setlow, J. K. et al., eds., Plenum Publishing, Vol. 8, pp. 277–297). See, also, U.S. Pat. No. 4,745,051 and U.S. Pat. No. 4,879,236. These systems are also successful in producing exo⁻Pfu DNA polymerase.

A preferred DNA segment containing a gene that encodes an exo⁻Pfu DNA polymerase is present on the plasmid pJCF72-1, pJCF72-2 and pJCF72-3.

Thus, the invention also contemplates DNA segments that encode an exo⁻Pfu DNA polymerase protein of this invention. DNA molecules, such as plasmids and bacteriophage genomes containing a DNA segment, are also a part of this invention. Host cells containing a plasmid, DNA segment, DNA molecule or bacteriophage genome of this invention are also contemplated.

The recombinant DNA molecules of the present invention are typically introduced into host cells, via a procedure commonly known as transformation or transfection. Transformation of appropriate host cells with a recombinant DNA molecule of the present invention is accomplished by well known methods that typically depend on the type of vector used. With regard to transformation of procaryotic host cells or other cells that contain substantial cell wall barriers, see, for example, Cohen et al., *Proc. Natl. Acad. Sci. USA*, 69:2110 (1972); and Maniatis et al., *Molecular Cloning, A Laboratory Manual*, Cold Spring Harbor Laboratory, Cold Spring Harbor, N.Y. (1982). With regard to transformation of vertebrate cells with retroviral vectors containing rDNA, see, for example, Sorge et al., *Mol. Cell. Biol.*, 4:1730–37 (1984); and Wigler et al., *Proc. Natl. Acad. Sci. USA*, 76:1373–76 (1979) .

Infection with Agrobacterium tumefaciens (Shaw, C. H., et al., *Gene*, (1983) 23:315) is used for certain plant cells. For mammalian cells without cell walls, the calcium phosphate precipitation method of Graham and van der Eb, *Virology* (1978) 52:546 is preferred. Transformations into yeast are carried out according to the method of Van Solingen, P., et al., *J. Bact.* (1977) 130:946 and Hsiao, C. L., et al., *Proc. Natl. Acad. Sci. (USA).*, (1979) 76:3829.

In addition to the transformed host cells themselves, cultures of the cells are contemplated as within the present invention. The cultures include monoclonal (clonally homogeneous) cultures, or cultures derived from a monoclonal culture, in a nutrient medium. Nutrient media useful for culturing transformed host cells are well known in the art and can be obtained from several commercial sources. In embodiments wherein the host cell is mammalian, a "serum-free" medium is preferably used.

The present method entails culturing a nutrient medium containing host cells transformed with a recombinant DNA molecule of the present invention that is capable of expressing a gene encoding a subject polypeptide. The culture is maintained for a time period sufficient for the transformed cells to express the subject polypeptide. The expressed polypeptide is then recovered from the culture.

Once a gene has been expressed in high levels, a DNA fragment containing the entire expression assembly, e.g., promoter, ribosome-binding site, and fusion protein gene) may be transferred to a plasmid that can attain very high copy numbers. For instance, the temperature-inducible "runaway replication" vector pKN402 may be used. Preferably, the plasmid selected will have additional cloning sites which allow one to score for insertion of the gene assembly. See, Bittner et al. *Gene*, 15:31 (1981). Bacterial cultures transformed with the plasmids are grown for a few hours to increase plasmid copy number, e.g., to more than 1000 copies per cell. Induction may be performed in some cases by elevated temperature and in other cases by addition of an inactivating agent to a repressor. Potentially very large increases in cloned exo⁻Pfu DNA polymerase can be obtained in this way.

The present invention further contemplates a recombinant DNA (rDNA) that includes a exo⁻Pfu DNA polymerase-encoding DNA segment of the present invention operatively linked to a vector for replication and/or expression. Preferred rDNA molecules contain less than 50,000 nucleotide base pairs, usually less than 20,000 base pairs and preferably less than about 10,000 base pairs. Preferably, a exo⁻Pfu DNA polymerase-encoding DNA of this invention is in the form of a plasmid, cosmid or phage.

A preferred rDNA molecule includes a nucleotide sequence shown in SEQ ID NO 2 from nucleotide base 224 to base 2548, but having one or more nucleotide substitutions according to the present invention to provide the required exonuclease deficiency in the coded Pfu DNA polymerase.

A rDNA molecule of the present invention can be produced by operatively linking a vector to a DNA segment of the present invention.

As used herein, the term "vector" refers to a nucleic acid molecule capable of transporting between different genetic environments another nucleic acid to which it has been operatively linked Preferred vectors are those capable of autonomous replication and/or expression of nucleic acids to which they are operatively linked are referred to herein as "expression vectors" . As used herein, the term "operatively linked", in reference to DNA segments, describes that the nucleotide sequence is joined to the vector so that the sequence is under the transcriptional and translation control of the expression vector and can be expressed in a suitable host cell.

As is well known in the art, the choice of vector to which a protein encoding DNA segment of the present invention is operatively linked depends upon the functional properties desired, e.g., protein expression, and upon the host cell to be transformed. These limitations are inherent in the art of constructing recombinant DNA molecules. However, a vector contemplated by the present invention is at least capable of directing the replication, and preferably also expression, of a gene operatively linked to the vector.

In preferred embodiments, a vector contemplated by the present invention includes a procaryotic replicon, i.e., a DNA sequence having the ability to direct autonomous replication and maintenance of the recombinant DNA molecule extrachromosomally in a procaryotic host cell, such as a bacterial host cell, transformed therewith. Such replicons are well known in the art. In addition, those embodiments that include a procaryotic replicon may also include a gene whose expression confers a selective advantage such as amino acid nutrient dependency or drug resistance to a bacterial host transformed therewith as is well known, in order to allow selection of transformed clones. Typical bacterial drug resistance genes are those that confer resistance to ampicillin, tetracycline, or kanamycin.

Those vectors that include a procaryotic replicon may also include a procaryotic promoter capable of directing the expression (transcription and translation) of the gene transformed therewith. A promoter is an expression control element formed by a DNA sequence that permits binding of RNA polymerase and transcription to occur. Promoter sequences compatible with bacterial hosts are typically provided in plasmid vectors containing convenient restriction sites for insertion of a DNA segment of the present invention. Bacterial expression .systems, and choice and use of vectors in those systems is described in detail in "Gene Expression Technology", *Meth. Enzymol.*, Vol 185, Goeddel, Ed., Academic Press, N.Y. (1990).

Expression vectors compatible with eucaryotic cells, preferably those compatible with vertebrate cells, can also be used to form the recombinant DNA molecules of the present invention. Eucaryotic cell expression vectors are well known in the art and are available from several commercial sources. Typically, such vectors are provided containing convenient restriction sites for insertion of the desired gene. Typical of such vectors are pSVL and pKSV-10 (Pharmacia), pBPV-1/pML2d (International Biotechnologies, Inc.), and pTDT1 (ATCC, #31255).

In preferred embodiments, the eucaryotic cell expression vectors used to construct the recombinant DNA molecules of the present invention include a selectable phenotypic marker that is effective in a eucaryotic cell, such as a drug resistance selection marker or selective marker based on nutrient dependency. A preferred drug resistance marker is the gene whose expression results in neomycin resistance, i.e., the neomycin phosphotransferase (neo) gene. Southern et al., *J. Mol. Appl. Genet.*, 1:327–341 (1982).

A DNA segment defining an exo⁻Pfu DNA polymerase of this invention can be prepared by a variety of molecular biological techniques. The precise nucleotide sequence is not critical so long as the resulting encoded protein has the requisite properties, and preferably encodes a preferred amino acid residue sequence as described herein.

In one approach, a DNA segment can be assembled by the systematic hybridization and ligation of synthetic oligonucleotides to form the complete DNA segment.

Synthetic oligonucleotides may be prepared by a variety of chemical synthetic means, such as using the triester method of Matteucci, et al., (*J. Am. Chem. Soc.*, (1981) 103:3185–3191) or using automated synthesis methods.

For portions of vectors derived from cDNA or genomic DNA that require sequence modifications as described herein to form the exonuclease deficient polymerase, site-specific primer-directed mutagenesis is used as described herein. This technique is now standard in the art, and is conducted using a primer synthetic oligonucleotide complementary to a single-stranded phage DNA to be mutagenized except for limited mismatching, representing the desired mutation. Briefly, the synthetic oligonucleotide is used as a primer to direct synthesis of a strand complementary to the phage, and the resulting double-stranded DNA is transformed into a phage-supporting host bacterium. Cultures of the transformed bacteria are plated in top agar, permitting plaque formation from single cells that harbor the phage.

Theoretically, 50% of the new plaques will contain the phage having, as a single strand, the mutated form; 50% will have the original sequence. The plaques are transferred to nitrocellulose filters and the "lifts" hybridized with kinased synthetic primer at a temperature that permits hybridization of an exact match, but at which the mismatches with the original strand are sufficient to prevent hybridization. Plaques that hybridize with the probe are then picked and cultured, and the DNA is recovered.

Host strains useful in cloning and expression are as follows:

For cloning and sequencing, and for expression of constructions under control of most bacterial promoters, *E. coli* strain MM294 obtained from *E. coli* Genetic Stock Center GCSC #6135, is particularly useful. For expression under control of the $P_L N_{RBS}$ promoter, *E. coli* strain K12 MC1000 lambda lysogen, $N_7 N_{53c} I857$ SusP$_{80}$ (ATCC 39531), may be used. Also useful is *E. coli* DG116, (ATCC 53606).

For M13 phage recombinants, *E. coli* strains susceptible to phage infection, such as *E. coli* K12 strain DG98, are employed. The DG98 strain has been deposited with ATCC Jul. 13, 1984 and has accession number 39768.

The thermostable, exonuclease deficient enzyme of this invention may be used for any purpose in which such enzyme is necessary or desirable. In a particularly preferred embodiment, the enzyme herein is employed in the cycle sequencing DNA amplification protocol set forth below.

EXAMPLES

In order that the invention described herein may be more fully understood, the following examples are set forth. It should be understood that the following examples are for illustrative purposes only and are not to be construed as limiting the invention.

1. Preparation of a Modified Vector for Expressing Exo-Pfu DNA Polymerase I

A. Cloning the Gene that Encodes Pyrococcus furiosus (Pfu) DNA Polymerase I

Pyrococcus furiosus (DSM 3638) was grown as described by Bryant et al, *J. Biol. Chem.*, 264:5070–5079 (1989), with an additional supplement of 10 mM Na$_2$WO$_4$ as described in Example 9. Following harvesting by centrifugation, genomic DNA was isolated from the biomass using Stratagene's genomic DNA isolation kit according to manufacturer' instructions. The DNA was then randomly sheared by several passages through an eighteen gauge needle and the fragments were separated by sucrose gradient centrifugation. The size of the fragments present within the fractions of the sucrose gradient were next estimated by agarose gel electrophoresis. The fractions containing four to nine kilobase fragments were combined and ligated to EcoR1 linkers and the resulting inserts were ligated into EcoR1 cut Lambda Zap II vector (Stratagene, La Jolla, Calif.) to create a genomic *Pyrococcus furiosus* library. This library was plated with XL1-Blue *E. coli* (Stratagene) on LB plates. Plaque lifts were performed on Duralose nylon filters (Stratagene) to isolate individual bacteriophage Colonies containing a cloned insert.

Pfu DNA polymerase I had been purified from cultures of cell paste prepared from cultures of *P. furiosus* as described in Example 9. The resulting purified protein had been microsequenced to identify a amino terminal protein sequence that was used to design a series of degenerate oligonucleotides corresponding to the microsequence. The oligonucleotides were used to probe the above library, and identify colonies containing a gene that encodes Pfu DNA polymerase I. Although several clones were identified, one clone containing the entire reading frame was selected and designated clone pLF72.

The insert of clone pLF72 was excised from the Lambda Zap II vector to form in the plasmid expression vector pBluescript (Stratagene) a vector designated pF72.

The insert of clone pF72 was sequenced on both strands using Sequenase™ (USB) and custom oligonucleotide primers using a primer walking strategy. The nucleotide sequence of the insert containing the native polymerase gene is shown in SEQ ID NO 2 from nucleotide bases 224 to 2548, and consists of a 2265 bp DNA segment encoding 775 amino acids corresponding to a predicted 90,113 dalton protein. The corresponding 755 amino acid residue sequence of the wild type (native) Pfu DNA polymerase enzyme encoded by the cloned gene is shown in SEQ ID NO 2.

B. Preparation of Exonuclease-Deficient Pfu DNA Polymerase I

Certain nucleotide bases within the coding sequence of the gene of plasmid pF72 were mutated so as to effect a substitution of the encoded amino acid residues, thereby inactivating the 3'–5' exonuclease activity associated with native Pfu DNA polymerase I without significantly affecting the DNA polymerase activity of the enzyme.

Site-directed mutagenesis of pF72 was conducted using the oligonucleotide-directed in vitro mutagenesis method according to Kunkel, Proc. Natl. Acad. Sci. USA, 82:488–492 (1985), and Kunkel et al., Meth. Enzymol., 4:367–382 (1987). For the substitution of Pfu DNA polymerase I residues $Asp^{141}$ and $Glu^{143}$ to insert Ala in their place, the following oligonucleotide #748 (SEQ ID NO 3) was synthesized using standard oligonucleotide synthesis:

5'-CTTGCCTTCGCTATAGCAACCCTCTAT-3'

Thereafter, single stranded template was prepared by first transforming E. coli strain CJ236 with the plasmid pF72. CJ236 has the genotype dut, ung, thi, relA;pCJ105 $Cm_r$. The transformants were grown overnight at 37C on chloramphenicol plus ampicillin plates. A single colony was used to inoculate 20 ml of LB plus chloramphenicol, and cultured overnight. One ml of the overnight culture was used to inoculate 50 ml of 2xYT media containing ampicillin. This culture was grown to an $O.D._{600nm}$ of 0.3. Thereafter, helper phage, VCSM13 (Stratagene) was added to the culture at a M.O.I. of 20 and further incubated at 37 C. for 1 hr. Then, 70 ul of kanamycin was added to the culture at 50 mg/ml and further incubated overnight at 37 C. The overnight culture was then centrifuged at 17,000xg for 15 min, the resulting supernatant transferred to a fresh microfuge tube, recentrifuged and transferred to a fresh microfuge tube, whereupon $MgCl_2$ was added to 5 mM. Thereafter, 150 ug RNase and 10 units of DNase were added to the supernatant, and the admixture was incubated for 1 hr at 37 C. Phagemids in the incubated admixture were precipitated by the addition of ¼ volume of 3.5 M $NH_4OAc$ in 20% PEG followed by an incubation on ice for 30 min and centrifugation at 17,000xg for 15 min. The pellet was recovered and dissolved in high salt buffer (300 mM NaCl,100 mM Tris, pH 8.0, 1 mM EDTA). The dissolved pellets were chilled on ice for 30 min, and centrifuged to remove debris. The resulting supernatant was phenol extracted, and the extracted nucleic acid was precipitated by addition of 1/10 volume of 7.8 M $NH_4OAc$ and 2 volumes of EtOH, incubation at −80° C. for 30 min, and 15 min centrifugation at 17,000xg. The resulting nucleic acid pellet is resuspended in 20 ul TE to form dissolved single-stranded uracil-containing DNA.

The single-stranded (ss) uracil-containing DNA was then mutagenized following the Kunkel method according to the protocol of the BioRad Muta-Gene manual (BioRad, Cailf.). The mutagenizing oligonucleotide (#748) was phosphorylated and then annealed to the ss uracil-containing DNA template, complementary (mutant) strand was synthesized using T4 DNA polymerase, and closed circular double-stranded (ds) DNA was formed by the addition of T4 DNA ligase. The mutagenesis reaction product was used to transform E. coli strain RR1. The resulting transformants were characterized by assaying for both polymerase and exonuclease activities described herein, and were also assessed for capacity to sequence DNA.

As described herein, the clone designated pJCF72-1, produced using oligonucleotide #748, was determined to retain 100% of its DNA polymerase activity, and possess essentially no exonuclease activity when compared to wild type Pfu DNA polymerase I.

pJCF72-1 contains nucleotide substitutions such that the coded enzyme contains the alanine residues in place of the residues $Asp^{141}$ and $Glu^{143}$ of wild type Pfu DNA polymerase I. This enzyme construct is referred to as an exonuclease deficient, or $exo^{31}$, Pfu DNA polymerase I, or $Ala^{141}$, $Ala^{143}$-Pfu DNA polymerase I Additional exo‾enzymes are prepared according to the present invention by introducing other mutations into the wild-type enzyme. For, example, using the above mutagenesis methods, vector pJCF72-2 encoding $Ala^{214}$, $Ala^{215}$-Pfu DNA polymerase I can be prepared Similarly, vector pJCF72-3 encoding $Ala^{311}$, $Ala^{315}$-Pfu DNA polymerase I has been prepared. Both pJCF72-2 and -3 express an exo‾ Pfu DNA polymerase of this invention.

Purification of Exo‾Pfu DNA Polymerase I

A. Cell growth and fermentation

The plasmid (pJCF72-1) encoding an exo‾ mutant gene for Pyrococcus furiosus DNA polymerase was freshly transformed into E. coli strain BL21/DE3/pLysS. A one liter overnight culture from a single colony transformant was grown in NZY containing 100 ug/ml ampicillin. The overnight culture was used to inoculate 12 1-liter shaker flasks containing NZY and 100 ug/ml ampicillin. The cells were grown for 24 hours, chilled, harvested at 3500 rpm for 20 minutes, and the cell pellet frozen at −20° C. until ready for lysis.

B. Cell Lysis

The lysis protocols were all carried out at 4° C. Fifty grams of frozen cell pellet prepared as described in Example 2A was transferred to a stainless steel beaker, and the cells were resuspended using 3 volumes (150 mls) of Lysis Buffer A (50 mM Tris-Cl, pH 8.2, 1 mM EDTA, 10 mM b-mercaptoethanol and 200 ug/ml lysozyme). The cell suspension was then incubated on ice for 60 min. Thereafter, the suspension was sonicated 7 times for 4 min each at 4° C. The sonicated suspension (lysate) was then transferred to 35 ml centrifuge tubes and centrifuged for 30 min a 13,000 rpm at 4° C. in a Sorvall RC-5B using a Sorvall SS-34 rotor. The resulting supernate, designated Fraction I, was collected and the volume measured.

Thereafter, Fraction I was transferred to a 1000 ml Erlenmeyer flask and heat-treated at 72° C. for 10 min using a water bath. Following heat treatment, Fraction I was transferred to 35 ml centrifuge tubes and centrifuged as before in the Sorvall rotor. The resulting supernatant, designated Fraction II, was collected, and the volume measured.

C. Protein Purification of Exo‾Pfu DNA Polymerase I

Fraction II was loaded directly onto a 5×10 cm Q-Sepharose column containing about 196 ml of chromatography matrix, after the column had been pre-equilibrated with Buffer B at a flow rate of about 5 ml/min. Buffer B contains 50 mM Tris-Cl, pH 8.2, 1 mM EDTA and 10 mM b-mercaptoethanol. The column was then was then washed with Buffer B until the $O.D._{280nm}$ approached baseline. During the loading and washing steps, the pass-through and the wash buffers off the column were collected and pooled to form Fraction III.

Fraction III was loaded directly onto a 2.6×40 cm P-11 column of about 200 ml matrix volume that had been pre-equilibrated with Buffer C at a flow rate of about 1 ml/min. Buffer C contains 50 mM Tris-Cl, pH 7.5, 1 mM EDTA and 10 mM b-mercaptoethanol. The column was then washed with 10 volumes of Buffer C, and then was eluted with a 2×500 ml gradient from 0.0 to 700 mM KCL in Buffer C. 10 ml fractions were collected throughout the procedure including loading, washing and eluant pass through, and were each fraction was assayed for DNA polymerase I activity as described herein.

Fractions collected off the P-11 column containing the peak DNA polymerase I activity were located in the eluant fractions, and were pooled and dialyzed overnight two times against 4 liters of Buffer D (10 mM $KPO_4$, pH 7.5, 5 mM b-mercaptoethanol, 5% (v/v) glycerol, 0.2% (v/v) NP-40, 0.2% (v/v) Tween 20 and 0.5M NaCl). Thereafter, the dialysate was collected, designated Fraction IV, and the volume recorded.

Fraction IV was then loaded onto a 2.6×23.5 cm ceramic hydroxyapatite (HA) column having a matrix of about 125 ml that was pre-equilibrated with Buffer D at a flow rate of 2.0 ml/min. Thereafter, the column was washed with Buffer D, and then was eluted with a 2×500 ml gradient from 10 to 400 mM $KPO_4$. Load, wash and eluant pass through fractions of 10 ml each were collected, and were each assayed for DNA polymerase I activity as before. The peak fractions containing activity were pooled and dialyzed overnight against 1 liter of Buffer E (50 mM Tris-Cl, pH 8.2, 0.1 mM EDTA, 1 mM DTT, 50% (v/v) glycerol, 0.1% (v/v) NP-40 and 0.1% (v/v) Tween 20). The dialysate was collected that contains purified exo⁻Pfu DNA polymerase I, the volume was measured, and the dialysate was stored at −20° C.

3. Assay for Pfu DNA Polymerase I Activity

The collected fractions were separately assayed for DNA polymerase I activity. An aliquot of a fraction was admixed and incubated for 30 minutes at 72° C. in 25 ul of a mixture containing 20 mM Tris-Cl, pH 7.5, 8 mM $MgCl_2$, 40 ug/ml BSA, 0.5 units activated calf thymus DNA (Pharmacia), 30 uM dATP, 30 uM dGTP, 30 uM dCTP, 3 uM TTP, and 1 uCi of $^3$H-TTP. Reactions were terminated on ice and 5 ul aliquots of the samples spotted on DEAE paper disks (DE-81, Whatman). The spotted disks were allowed to dry and washed three times in 2× SSC (1× SSC is 0.3M NaCl, 0.03M NaCitrate) for five minutes each, then washed for one minute in 100% cold ethanol, and dried. The incorporated $^3$H-TTP was counted with an efficiency of 55% in a liquid scintillation system. One unit of polymerase activity catalyzes the incorporation of 10 nmol total nucleotide into a DEAE-precipitable form in 30 minutes at 72° C.

4. Exonuclease 3' to 5' Activity Assays

The 3' to 5' exonuclease activity of purified Pfu DNA polymerase I, prepared in Example 2, was assayed. To that end, a sample containing 0.01 to 0.1 unit of DNA polymerase activity was admixed in a 25 ul exonuclease reaction admixture containing 40 mM Tris-Cl, pH 7.5, 10 mM $MgCl_2$, 2.5 ug of Taq I restriction endonuclease-digested Lambda DNA fragments filled in with $^3$H-dGTP and $^3$H-dCTP. The labelled DNA substrate was prepared by digesting 1 mg lambda gt10 with 1000 units Taq I at 68° C. for 3 hrs in 1X Universal Buffer (Stratagene), followed by filling in the 3' recessed ends with 25 uCi each of $^3$H-dGTP and $^3$H-dCTP using 50 units of Sequenase (USB; United States Biochemicals, Inc.); the labelled fragments were separated from unincorporated nucleotides by passage through a NucTrap column (Stratagene) following the manufacturer's instructions. After a 30 min incubation of the endonuclease reaction admixture at 72° C., the reaction was terminated by addition of 5 ul of 15 mg/ml BSA and 13 ul of 50% trichloroacetic acid, and incubated on ice for 30 min to precipitate the nucleic acids. The precipitated nucleic acids were then centrifuged at 9000×g for 5 min, and 25 ul of the resulting supernatant was removed for scintillation counting. All reactions were performed in triplicate. One unit of exonuclease activity catalyzes the acid solubilization of 10 nmole of total nucleotides in 30 min at 72° C.

Exo⁻Pfu DNa polymerase I prepared and purified as described in Examples 1 and 2 was assayed for DNA polymerase I activity and for 3'–5' exonuclease activity as described in Examples 3 and 4. The results are shown in Table 1 below.

TABLE 1

| Enzyme | Specific Activity[a] | | Pol/Exo Ratio |
| | Polymerase | Exonuclease | |
| --- | --- | --- | --- |
| wt Pfu Pol | 13.5 KU/mg | 340 U/mg | 39 |
| rPfu Pol | 16.1 KU/mg | 480 U/mg | 34 |
| exo⁻Pfu Pol | 28.6 KU/mg | 8 U/mg | 3575 |

[a]DNA polymerase I activity and 3'–5' exonuclease activity were determined as described in Examples 3 and 4, respectively, and are expressed as specific activity (KU is thousands of units). Wild type (wt) and recombinant (r) Pfu DNA polymerase were prepared as described in Example 1. The exo⁻Pfu DNA polymerase I tested in Table 1 is from clone pJCF72-1.

The data in Table 1 shows that only background levels of 3'–5' exonuclease activity can be detected in the mutant enzyme, although significant DNA polymerase activity is present.

5. Incorporation of Thiolated Nucleotides

To determine the relative efficiency of $^{35}$S-dATP analog (thiolated nucleotide) incorporation during DNA polymerase reactions, equal amounts (one unit) of specific activity of exo⁻Pfu DNA polymerase I and Taq DNA polymerase were used (as determined by the polymerase assay in Example 3) in the polymerase assay described in Example 3, except that $^3$H-dTTT was replaced with $^{35}$S-dATP. Following incubation at 72° C. for 30 min, DEAE precipitable counts were determined as before. The relative incorporation efficiencies of Taq vs Pfu DNA polymerases for the thiolated analog were thereby determined, and the results are shown in Table 2.

TABLE 2

| Enzyme | Acid-Precipitable $^{35}$S-dATP CPM |
| --- | --- |
| Taq DNA Pol | 21,704 cpm/min |
| Exo⁻Pfu DNA Pol | 171,761 cpm/min |

The data in Table 2 shows that exo⁻Pfu DNA polymerase I incorporates the thiolated analog about 8 times more efficiently than Taq DNA polymerase.

6. Cycle-Sequencing Using Exo⁻Pfu Polymerase

Exo⁻Pfu DNA polymerase I was used in cycle-sequencing reactions to generate DNA sequence data from a variety of DNA templates. Briefly, a cycle sequencing reaction mixture was prepared containing 20 mM Tris-Cl, pH 8.8, 10 mM KCl, 6 mM $(NH_4)_2SO_4$, 2 mM $MgCl_2$, 0.1% Triton X-100, 100 ug/ml bovine serum albumin (BSA), 2 uM dATP, 5 uM dCTP, 5 uM dGTP, 5 uM dTTP, 0.16 nanograms (ng) per ml primer (oligonucleotide of sequence 5' -GTAAAACGACG-GCCAGT-3')(SEQ ID NO:4), 2.5 units exo⁻Pfu DNA polymerase, 10 uCi labelled dATP (1000–5000 Ci/mmole), 50–400 femptomoles (fm) pBluescript template and 13% (v/v) DMSO (added last to the sequencing reaction admixture). $^{35}$SdATP, $^{32}$P-dATP or $^{33}$P-dATP were used as the labeled dATP. The reaction admixture in 30 ul was denatured by heating 5 min at 95° C., then cycled 30 times as follows: 95° C. for 20 seconds, 60° C. for 30 sec, 72° C. for 40 sec, using a Perkin-Elmer Cetus 9600 thermal cycler without oil overlay. Thereafter, the reaction was stopped by adding 5 ul of stop dye solution (95% formamide, 20 mM EDTA, 0.05% bromophenol blue and 0.05% xylene cyanol). The stopped reaction was then heated to 80° C. for 5 min immediately prior to loading on a sequencing gel.

Polyacrylamide sequencing gels were prepared (6% gel having 5.7% acrylamide/0.3% bis-acrylamide/7M Urea/1X TBE), preheated to 50° C. using a power supply regulated to 120 watts (W). The denatured sample (2 ul) was loaded onto the gel and electrophoresed at 50° C until the bromophenol blue dye front migrated to the bottom of the gel. The gell assembly was taken apart, the gel transferred to Whatmann 3 MM paper, dried and exposed to X-ray film for 12–20 hrs.

The resulting sequencing gels are shown in FIG. 1 comparing cycle-sequencing results using Taq, Vent and exo⁻Pfu DNA polymerases. The results show high quality DNA sequencing ladders for all three enzymes when $^3$H-dTTP is used. In addition, the results show that Taq DNA polymerase cannot produce sequencing ladders when thiolated dATP is used, whereas both wt and exo⁻Pfu DNA polymerase I produce good sequencing ladders in a cycle-sequencing reaction. Similar results were observed when the template used was a PCR reaction product, namely a DNA fragment of about 550 bases in length.

PCR amplification of specific fragments was run using exo⁻Pfu DNA polymerase I, in which the procedures were identical to normal PCR with Taq or wt Pfu DNA polymerases. Thus, the exo⁻Pfu DNA polymerase can be used in conventional PCR.

Cycle sequencing is becoming the method of choice for sequencing in many applications because it allows sequencing of very small amounts of template DNA, such as can be produced in a PCR reaction.

7. Molecular Weight Determination

Figure 2:
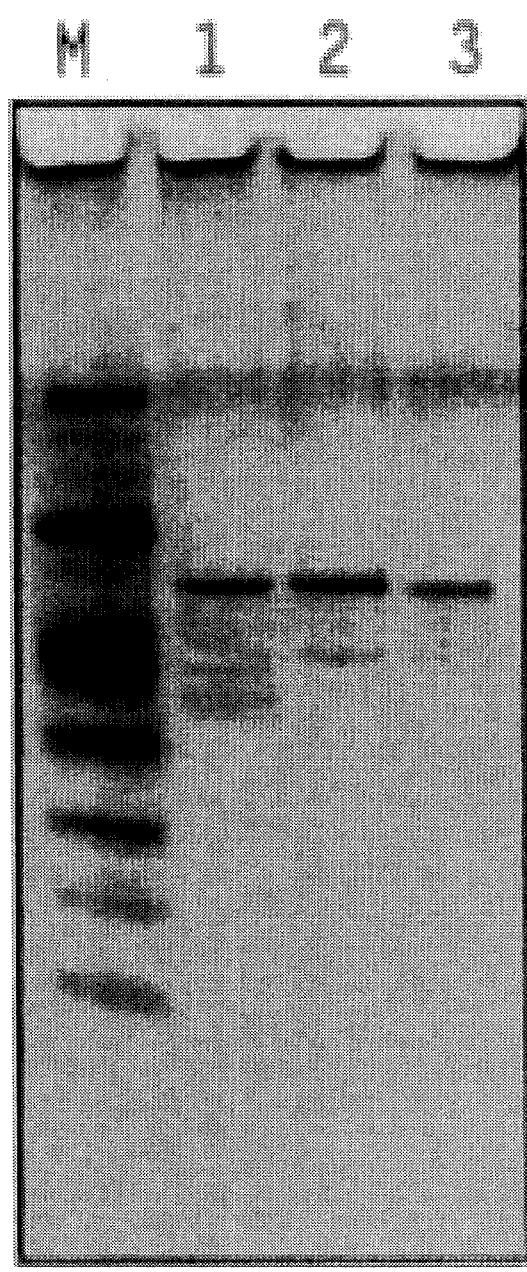
FIG. 2 illustrates the molecular weight determination of exo⁻Pfu DNA polymerase compared to wt (native, purified) and recombinant Pfu DNA polymerase as described in Example 7 using denaturing SDS-PAGE analysis (12% gel, under reducing conditions, i.e., DTT). Low molecular weight standards (Biorad) are electrophoresed in lane M. The molecular weights of the standards are 97,400 daltons (phosphorylase B), 66,200 daltons (bovine serum albumin), 42,699 daltons, 31,000 daltons, 21,500 daltons, and 14,400 daltons. In lanes 1, 2 and 3, Pfu DNA polymerase I is shown for the wt, recombinant and exo⁻varieties, respectively, and all exhibit a molecular weight of about 90,000– 93,000 daltons.

The molecular weight of the purified exo⁻Pfu DNA polymerase prepared in Example 2 was determined by SDS-PAGE under denaturing conditions according to the method of Laemmli et al., *J. Mol. Biol.*, (1973) 80:575–599. Samples of wt (native, purified), recombinant and exo⁻Pfu DNA polymerases, and molecular weight markers were applied to a 12% gel, 1 mm thick, SDS-polyacrylamide gel (Novex, Encinitas, CA) and electrophoresed in a running buffering containing 1% SDS, 2.4 mM Tris, and 18 mM Glycine. The gel was silver-stained to visualize the proteins. The results of that analysis, shown in FIG. 2, indicate that exo⁻Pfu DNA polymerase migrates at the same molecular weight as wt or recombinant Pfu DNA polymerase. That mobility compared to the markers yields a relative molecular weight of 90,000–93,000 daltons.

8. Thermostability of Exo⁻Pfu DNA Polymerase

The thermostability of exo⁻Pfu DNA polymerase was compared to other DNA polymerases by subjecting the enzyme in the DNA polymerase reaction buffer of Example 3 to 95° C. for 1 hr prior to the addition of nucleic acid template to the reaction admixture. Under these temperature conditions, both wt Pfu DNA polymerase I and exo⁻Pfu DNA polymerase retained 95% of the specific activity initially present, whereas Vent DNA polymerase, Circum-Vent DNA polymerase and Taq DNA polymerase retained only up to 70% of the specific activity initially present, after the 95° C. heat treatment.

Thus, the temperature stability of exo⁻Pfu DNA polymerase provides extended utility when used in reactions requiring multiple high temperature steps such as cycle-sequencing and PCR.

9. Purification of Native Pfu DNA Polymerase

A. Culturing of Pyrococcus furiosus and Preparation of Pfu Cell Paste

The following describes how the hyperthermophilic archaebacterium, *P. furiosus*, is routinely grown in a 500 liter fermentor for the purpose of obtaining cell mass in sufficient quantities for large scale protein purification. It is a modified version [Bryant et al., *J. Biol. Chem.*, 264:5070–5079 (1989)] of the original protocol of Fiala et al., *Arch. Microbiol.*, 145:56–61 (1986).

*P. furiosus* is available from Dentsche Sammlung Von Microorganismen (DSM), Grise-Bach StraSSE 8, d-3400 Göttengen, FRG, under the accession number DSM-6217.

For culture maintenance, *P. furiosus* (DSM 3638) is routinely grown at 85° C.–88° C. as a closed static culture in 100 ml of the medium described in Table 3.

TABLE 3

| Maltose | 5 g/l |
|---|---|
| NH$_4$Cl | 1.25 g/l |
| Elemental Sulfur | 5 g/l |
| Na$_2$S | 0.5 g/l |
| Synthetic Sea Water$^1$ | |
| Vitamin mixture$^2$ | 1 ml/l |
| FeCl$_3$ | 25 μM |
| Na$_2$WO$_4$ | 10 μM |
| Yeast Extract | 0.01% |

$^{(1)}$Synthetic Sea Water:
NaCl, 13.8 g/l
MgSO$_4$, 3.5 g/l
MgCl$_2$, 2.7 g/l
KCl, 0.3 g/l
CaCl$_2$, 0.75 g/l
KH$_2$PO$_4$, 0.5 g/l
NaBr, 0.0–5 g/l
KI, 0.05 g/l
H$_3$BO$_3$, 0.015 g/l
Sodium citrate, 0.005 g/l
$^{(2)}$Vitamin mixture [Balch et al., Microbiol. Rev., 43:260–296 (1979)]:
Biotin, 2 mg/l
Folic acid, 2 mg/l
Pyridoxine hydrochloride, 10 mg/l
Thiamine hydrochloride, 5 mg/l
Riboflavin, 5 mg/l
Nicotinic acid, 5 mg/l
DL-Calcium pantothenate, 5 mg/l
Vitamin B$_{12}$, 0.1 mg/l
p-Aminobenzoic acid, 5 mg/l
Lipoic acid, 5 mg/l Growth is monitored by the increase in turbidity at 600 nm. Cells can be stored in the same medium at 4° C. and remain viable for at least a year, although periodic transfer is recommended. Large scale (preparative) growth of *P. furiosus* was performed as follows: Growth medium according to Table 3, was prepared, except that the sulfide was replaced with titanium (III) nitrilotriacetate [final concentration, 30 μM as described in Moench et al., *J. Microbiol. Meth.*, 1:199–202 (1983)]and the elemental sulfur is omitted. The medium was then sparged with Argon (Ar).

A two liter flask was inoculated with two 100 ml cultures. The two liter culture was used as an inoculum for a 20 liter culture. Two 20 liter cultures were used to inoculate a 500 liter culture. The culture was maintained at 88° C., bubbled with Ar (7.5 liters/min) and stirred at about 50 rpm. After about 20 hours (A$_{600}$~0.5) the cells were harvested with a Sharples continuous flow centrifuge at 100 liters/hour. The cells were frozen in liquid N2 immediately after harvesting. The yield of cells is typically 400–600 g wet weight.

It should be noted that *P. furiosus* has a fermentative type of metabolism and produces organic acids, $CO_2$ and $H_2$ as final products. $H_2$ production inhibits growth, so cultures have to be sparged with Ar (or any inert gas) to remove $H_2$. Alternatively, elemental sulfur may be added. In this case, the reductant that would otherwise be used to generate $H_2$ is used to reduce elemental sulfur to $H_2S$. The addition of elemental sulfur is convenient for small scale cultures in glass vessels, but its reduction cannot be used to remove inhibitory $H_2$ in 500 liter stainless steel fermentors because of the corrosive nature of $H_2S$.

B. Lysis of Pf Cell Paste

Fifty grams (g) of Pf cell paste prepared in Example 9A were thawed at room temperature. Two hundred milliliters (ml) of lysis buffer consisting of 50 millimolar (mM) Tris-HCl, pH 8.2, 10 mM beta mercaptoethanol, 1 mM EDTA and 200 microgram/ml (µg/ml) of lysozyme were admixed to the thawed cell paste. The admixture was thereafter maintained for 30 minutes at room temperature. The maintained admixture was processed in a French press for two cycles. The cell lysate was sonicated for 10 minutes at room temperature and centrifuged at 16,000 RPM in a SA600 rotor for 60 minutes at room temperature and the supernatant recovered.

C. Column Chromatography of Pf Cell Lysate

The supernatant prepared in Example 9B was loaded on to a Q-sepharose (2.5×40 centimeter) column at room temperature. The column containing the cell lysate supernatant was then washed with 200 ml of column buffer (50 mM Tris-HCl, pH 8.2, 10 mM beta mercaptoethanol and 1 mM EDTA). The column pass through and the washes were collected, pooled, and then centrifuged at 9000×g in a Sorvall GS3 rotor at room temperature to remove any insoluble material.

The resulting supernatant, containing partially purified Pfu DNA polymerase, was recovered from the pellet and loaded directly onto a phosphocellulose column (2.5×40 cm) at room temperature. The column was washed with column buffer to remove any proteins that did not bind to the column until the optical density measured at an absorbance of 280 nm dropped to baseline. The immobilized Pfu DNA polymerase was thereafter eluted with a one liter linear gradient of NaCl ranging in concentration from 0M to 0.7M dissolved in column buffer and 10 ml fractions were collected.

The collected fractions were separately assayed for Pfu DNA polymerase activity using the procedure described in Example 3. The results of this assay indicated that the peak fractions from the phosphocellulose column containing the highest concentration of Pfu DNA polymerase were eluted with 200 mM NaCl and that Pfu DNA polymerase constituted about 10% of the total protein present in those fractions.

D. FPLC Purification of Pfu DNA Polymerase

The fractions containing approximately 90% of the total DNA polymerase I activity as prepared and measured in Example 9C were pooled and dialyzed against column buffer overnight at 4° C. to form a NaCl-free Pfu DNA polymerase solution. The dialyzed salt-free Pfu DNA polymerase solution was loaded onto a Mono S HR 5/5 FPLC (fast phase liquid chromatography) column (Pharmacia, Piscataway, N.J.) previously equilibrated with the before-described column buffer. The Mono S column containing the Pfu DNA polymerase was washed with about four column volumes of column buffer prior to elution to remove any proteins that did not bind to the column. The immobilized proteins were eluted with a one liter linear gradient of NaCl ranging in concentration from 0.0M to 0.7M dissolved in column buffer.

Fractions were collected and assayed for the presence of FPLC purified Pfu DNA polymerase activity as described above. The results of this assay indicated that the peak fractions from the Mono S column containing the highest concentration of FPLC purified Pfu DNA polymerase were eluted with 120 mM NaCl. The fractions containing 90% of the peak FPLC purified Pfu DNA polymerase activity were pooled and dialyzed against the column buffer additionally containing 10% glycerol overnight at room temperature to form NaCl-free FPLC purified Pfu DNA polymerase.

The resultant purified and dialyzed Pfu DNA polymerase was then subjected to a final purification on a 1.5×20 cm Matrix gel Blue A column (Amicon, Danvers, Mass.). The Matrix gel Blue A column was first equilibrated with the before-described column buffer containing 10% glycerol, 0.1% Tween 20 (polyoxyethylenesorbitan monolaurate) and 0.1% non-idet P40. The purified and dialyzed Pfu DNA polymerase was then applied to the column using FPLC pumps. The column containing the Pfu DNA polymerase sample was then washed with two column volumes of the glycerol-containing column buffer to remove any proteins that did not bind to the column. The immobilized Pfu DNA polymerase was eluted from the column with a one liter linear gradient of KCl ranging in concentration from 0.0M to 0.7M KCl.

Eluted fractions from the Affi-gel column were collected and assayed for the presence of purified Pfu DNA polymerase activity as described previously. The fractions eluted with 200 to 300 mM KCl contained the peak Pfu DNA polymerase activity, with the optimal activity recovered at about 280 mM KCl. The peak fractions were pooled and concentrated through Centricon-30 columns which have a molecular weight cut-off at 30,000 kD (Amicon, Beverly, Mass.) to form a concentrated solution of purified Pfu DNA polymerase. The purified Pfu DNA polymerase was thereafter dialyzed against column buffer containing 50% glycerol to form KCl-free purified Pfu DNA polymerase. The resultant salt-free Pfu DNA polymerase was determined to be about 95% homogeneous.

The foregoing is intended as illustrative of the present invention but not limiting. Numerous variations and modifications can be effected without departing from the true spirit and scope of the invention.

What is claimed is:

1. A recombinant thermostable *Pyrococcus furiosus* DNA polymerase I deficient in 3' to 5' exonuclease activity, wherein said polymerase has an amino acid residue sequence represented by the formula shown in SEQ ID NO 1 from residue 1 to residue 775, with the exception of an amino acid residue substitution selected from the group consisting of (1) $Ala^{141}/Ala^{143}$, (2) $Ala^{214}/Ala^{215}$, and (3) $Ala^{311}/Ala^{315}$.

2. The polymerase of claim 1 wherein said polymerase retains at least 95% of its DNA polymerase activity after exposure to 95° C. for 1 hour.

3. The polymerase of claim 1 wherein said polymerase has less than 50 units of specific 3' to 5' exonuclease activity per milligram of protein.

4. The polymerase of claim 1 wherein said polymerase has a ratio of specific activity of DNA polymerase activity to 3' to 5' exonuclease activity of at least 1000.

5. A plasmid containing a gene coding for a recombinant thermostable *Pyrococcus furiosus* DNA polymerase I deficient in 3' to 5' exonuclease activity, wherein said polymerase has an amino acid residue sequence represented by the formula shown in SEQ ID NO 1 from residue 1 to residue 775, with the exception of an amino acid residue substitution selected from the group consisting of (1) $Ala^{141}/Ala^{143}$, (2) $Ala^{214}/Ala^{215}$, and (3) $Ala^{311}/Ala^{315}$.

6. The plasmid of claim 5 wherein said polymerase has a ratio of specific activity of DNA polymerase activity to 3' to 5' exonuclease activity of at least 1000.

7. A procaryotic cell transformed with the plasmid of claim 5.

8. A bacteriophage containing a gene coding for a *Pyrococcus furiosus* DNA polymerase I deficient in 3' to 5' exonuclease activity, wherein said polymerase has an amino acid residue sequence represented by the formula shown in SEQ ID NO 1 from residue 1 to residue 775, with the exception of an amino acid residue substitution selected from the group consisting of (1) $Ala^{141}/Ala^{143}$, (2) $Ala^{214}/Ala^{215}$, and (3) $Ala^{311}/Ala^{315}$.

9. The bacteriophage of claim 8 wherein said polymerase has a ratio of specific activity of DNA polymerase activity to 3' to 5' exonuclease activity of at least 100.

* * * * *

UNITED STATES PATENT AND TRADEMARK OFFICE
CERTIFICATE OF CORRECTION

PATENT NO. : 5,489,523　　　　　　　　　　　　　Page 1 of 2

DATED : February 6, 1996

INVENTOR(S) : Mathur, Eric J.

It is certified that error appears in the above-indentified patent and that said Letters Patent is hereby corrected as shown below:

Through-out: "Taq" should read -- *Taq* -- (except when in parens "()")

Item [56] Cover Page, line 13, "Pyroccus" should read -- Pyrococcus --

Column 2, line 32, "$^{32}$p-" should read -- $^{32}$P- --

Column 2, line 46, "toy" should read -- to --

Column 7, line 25, "least. 98%" should read -- least 98% --

Column 8, line 9, "2-Hydroxy- 1" should read -- 2-hydroxy-1 --

Column 8, line 63, "in vitro" should read -- *in vitro* --

Column 10, line 26, "XL1Blue" should read -- XL1-Blue --

Column 11, line 31, "Agrobacterium tumefaciens" should read -- *Agrobacterium tumefaciens* --

Column 12, line 66, ".systems," should read -- systems, --

Column 15, line 18, "dut, ung, thi, relA;pCJ105 CM$_r$." should read -- *dut, ung, thi, relA;pCJ105 CM$_r$.* --

Column 16, line 3, "exo$^{31}$" should read -- exo· --

Column 16, line 9, "prepared Similarly," should read --prepared. Similarly, --

Coulmn 18, line 36, "Taq vs Pfu" should read -- *Taq* vs *Pfu* --

Coulmn 18, line 43, "Taq" should read -- *Taq* --

Coulmn 19, line 16, "Tag," should read -- *Taq*, --

UNITED STATES PATENT AND TRADEMARK OFFICE
CERTIFICATE OF CORRECTION

PATENT NO. : 5,489,523
DATED : February 6, 1996
INVENTOR(S) : Mathur, Eric J.

It is certified that error appears in the above-indentified patent and that said Letters Patent is hereby corrected as shown below:

Column 19, line 53, "8. Thermostability" should read -- (tab)8. Thermostability --

Column 20, line 6, "Pyrococcus furiosus" should read -- *Pyrococcus furiosus* --

Signed and Sealed this

Seventeenth Day of June, 1997

Attest:

Attesting Officer

BRUCE LEHMAN

*Commissioner of Patents and Trademarks*

SEQUENCE LISTING ( 1 ) GENERAL INFORMATION:

( i i i ) NUMBER OF SEQUENCES: 4

( 2 ) INFORMATION FOR SEQ ID NO:1:

-continued (i) SEQUENCE CHARACTERISTICS:
   (A) LENGTH: 775 amino acids
   (B) TYPE: amino acid
   (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:1:

```
Met Ile Leu Asp Val Asp Tyr Ile Thr Glu Glu Gly Lys Pro Val Ile
 1               5                  10                  15

Arg Leu Phe Lys Lys Glu Asn Gly Lys Phe Lys Ile Glu His Asp Arg
                20                  25                  30

Thr Phe Arg Pro Tyr Ile Tyr Ala Leu Leu Arg Asp Asp Ser Lys Ile
            35                  40                  45

Glu Glu Val Lys Lys Ile Thr Gly Glu Arg His Gly Lys Ile Val Arg
50                      55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Val Pro Thr Ile
                85                  90                  95

Arg Glu Lys Val Arg Glu His Pro Ala Val Val Asp Ile Phe Glu Tyr
                100                 105                 110

Asp Ile Pro Phe Ala Lys Arg Tyr Leu Ile Asp Lys Gly Leu Ile Pro
            115                 120                 125

Met Glu Gly Glu Glu Glu Leu Lys Ile Leu Ala Phe Asp Ile Glu Thr
130                     135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Val Ser Ser Glu Arg Glu Met Ile Lys
            180                 185                 190

Arg Phe Leu Arg Ile Ile Arg Glu Lys Asp Pro Asp Ile Ile Val Thr
            195                 200                 205

Tyr Asn Gly Asp Ser Phe Asp Phe Pro Tyr Leu Ala Lys Arg Ala Glu
210                     215                 220

Lys Leu Gly Ile Lys Leu Thr Ile Gly Arg Asp Gly Ser Glu Pro Lys
225                     230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
        290                 295                 300

Leu Glu Arg Val Ala Lys Tyr Ser Met Glu Asp Ala Lys Ala Thr Tyr
305                     310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Val Ala
```

|     |     |     |     |     | 355 |     |     |     |     | 360 |     |     |     |     | 365 |     |     |
| --- | --- | --- | --- | --- | --- | --- | --- | --- | --- | --- | --- | --- | --- | --- | --- | --- | --- |
| Pro | Asn | Lys | Pro | Ser | Glu | Glu | Glu | Tyr | Gln | Arg | Arg | Leu | Arg | Glu | Ser |
|     |     | 370 |     |     |     |     | 375 |     |     |     |     | 380 |     |     |     |
| Tyr | Thr | Gly | Gly | Phe | Val | Lys | Glu | Pro | Glu | Lys | Gly | Leu | Trp | Glu | Asn |
| 385 |     |     |     |     | 390 |     |     |     |     | 395 |     |     |     |     | 400 |
| Ile | Val | Tyr | Leu | Asp | Phe | Arg | Ala | Leu | Tyr | Pro | Ser | Ile | Ile | Ile | Thr |
|     |     |     |     | 405 |     |     |     |     | 410 |     |     |     |     | 415 |     |
| His | Asn | Val | Ser | Pro | Asp | Thr | Leu | Asn | Leu | Glu | Gly | Cys | Lys | Asn | Tyr |
|     |     |     | 420 |     |     |     |     | 425 |     |     |     |     | 430 |     |     |
| Asp | Ile | Ala | Pro | Gln | Val | Gly | His | Lys | Phe | Cys | Lys | Asp | Ile | Pro | Gly |
|     |     | 435 |     |     |     |     | 440 |     |     |     |     | 445 |     |     |     |
| Phe | Ile | Pro | Ser | Leu | Leu | Gly | His | Leu | Leu | Glu | Glu | Arg | Gln | Lys | Ile |
|     | 450 |     |     |     |     | 455 |     |     |     |     | 460 |     |     |     |     |
| Lys | Thr | Lys | Met | Lys | Glu | Thr | Gln | Asp | Pro | Ile | Glu | Lys | Ile | Leu | Leu |
| 465 |     |     |     |     | 470 |     |     |     |     | 475 |     |     |     |     | 480 |
| Asp | Tyr | Arg | Gln | Lys | Ala | Ile | Lys | Leu | Leu | Ala | Asn | Ser | Phe | Tyr | Gly |
|     |     |     |     | 485 |     |     |     |     | 490 |     |     |     |     | 495 |     |
| Tyr | Tyr | Gly | Tyr | Ala | Lys | Ala | Arg | Trp | Tyr | Cys | Lys | Glu | Cys | Ala | Glu |
|     |     |     | 500 |     |     |     |     | 505 |     |     |     |     | 510 |     |     |
| Ser | Val | Thr | Ala | Trp | Gly | Arg | Lys | Tyr | Ile | Glu | Leu | Val | Trp | Lys | Glu |
|     |     | 515 |     |     |     |     | 520 |     |     |     |     | 525 |     |     |     |
| Leu | Glu | Glu | Lys | Phe | Gly | Phe | Lys | Val | Leu | Tyr | Ile | Asp | Thr | Asp | Gly |
|     | 530 |     |     |     |     | 535 |     |     |     |     | 540 |     |     |     |     |
| Leu | Tyr | Ala | Thr | Ile | Pro | Gly | Gly | Glu | Ser | Glu | Glu | Ile | Lys | Lys | Lys |
| 545 |     |     |     |     | 550 |     |     |     |     | 555 |     |     |     |     | 560 |
| Ala | Leu | Glu | Phe | Val | Lys | Tyr | Ile | Asn | Ser | Lys | Leu | Pro | Gly | Leu | Leu |
|     |     |     |     | 565 |     |     |     |     | 570 |     |     |     |     | 575 |     |
| Glu | Leu | Glu | Tyr | Glu | Gly | Phe | Tyr | Lys | Arg | Gly | Phe | Phe | Val | Thr | Lys |
|     |     |     | 580 |     |     |     |     | 585 |     |     |     |     | 590 |     |     |
| Lys | Arg | Tyr | Ala | Val | Ile | Asp | Glu | Glu | Gly | Lys | Val | Ile | Thr | Arg | Gly |
|     |     | 595 |     |     |     |     | 600 |     |     |     |     | 605 |     |     |     |
| Leu | Glu | Ile | Val | Arg | Arg | Asp | Trp | Ser | Glu | Ile | Ala | Lys | Glu | Thr | Gln |
|     | 610 |     |     |     |     | 615 |     |     |     |     | 620 |     |     |     |     |
| Ala | Arg | Val | Leu | Glu | Thr | Ile | Leu | Lys | His | Gly | Asp | Val | Glu | Glu | Ala |
| 625 |     |     |     |     | 630 |     |     |     |     | 635 |     |     |     |     | 640 |
| Val | Arg | Ile | Val | Lys | Glu | Val | Ile | Gln | Lys | Leu | Ala | Asn | Tyr | Glu | Ile |
|     |     |     |     | 645 |     |     |     |     | 650 |     |     |     |     | 655 |     |
| Pro | Pro | Glu | Lys | Leu | Ala | Ile | Tyr | Glu | Gln | Ile | Thr | Arg | Pro | Leu | His |
|     |     |     | 660 |     |     |     |     | 665 |     |     |     |     | 670 |     |     |
| Glu | Tyr | Lys | Ala | Ile | Gly | Pro | His | Val | Ala | Val | Ala | Lys | Lys | Leu | Ala |
|     |     | 675 |     |     |     |     | 680 |     |     |     |     | 685 |     |     |     |
| Ala | Lys | Gly | Val | Lys | Ile | Lys | Pro | Gly | Met | Val | Ile | Gly | Tyr | Ile | Val |
|     | 690 |     |     |     |     | 695 |     |     |     |     | 700 |     |     |     |     |
| Leu | Arg | Gly | Asp | Gly | Pro | Ile | Ser | Asn | Arg | Ala | Ile | Leu | Ala | Glu | Glu |
| 705 |     |     |     |     | 710 |     |     |     |     | 715 |     |     |     |     | 720 |
| Tyr | Asp | Pro | Lys | Lys | His | Lys | Tyr | Asp | Ala | Glu | Tyr | Tyr | Ile | Glu | Asn |
|     |     |     |     | 725 |     |     |     |     | 730 |     |     |     |     | 735 |     |
| Gln | Val | Leu | Pro | Ala | Val | Leu | Arg | Ile | Leu | Glu | Gly | Phe | Gly | Tyr | Arg |
|     |     |     | 740 |     |     |     |     | 745 |     |     |     |     | 750 |     |     |
| Lys | Glu | Asp | Leu | Arg | Tyr | Gln | Lys | Thr | Arg | Gln | Val | Gly | Leu | Thr | Ser |
|     |     | 755 |     |     |     |     | 760 |     |     |     |     | 765 |     |     |     |
| Trp | Leu | Asn | Ile | Lys | Lys | Ser |
|     |     | 770 |     |     |     | 775 |

( 2 ) INFORMATION FOR SEQ ID NO:2:

( i ) SEQUENCE CHARACTERISTICS:
        ( A ) LENGTH: 3499 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: 5'UTR
        ( B ) LOCATION: 1..223

( i x ) FEATURE:
        ( A ) NAME/KEY: CDS
        ( B ) LOCATION: 224..2551

( i x ) FEATURE:
        ( A ) NAME/KEY: 3'UTR
        ( B ) LOCATION: 2552..3499

( x i ) SEQUENCE DESCRIPTION: SEQ ID NO:2:

```
CCCTGGTCCT GGGTCCACAT ATATGTTCTT ACTCGCCTTT ATGAAGAATC CCCCAGTCGC       60
TCTAACCTGG GTTATAGTGA CAAATCTTCC TCCACCACCG CCCAAGAAGG TTATTTCTAT      120
CAACTCTACA CCTCCCCTAT TTTCTCTCTT ATGAGATTTT AAGTATAGT TATAGAGAAG       180
GTTTTATACT CCAAACTGAG TTAGTAGATA TGTGGGGAGC ATAATGATTT AGATGTGGA       240
TTACATAACT GAAGAAGGAA AACCTGTTAT TAGGCTATTC AAAAAGAGA ACGGAAAATT       300
TAAGATAGAG CATGATAGAA CTTTTAGACC ATACATTTAC GCTCTTCTCA GGGATGATTC      360
AAAGATTGAA GAAGTTAAGA AATAACGGG GGAAAGGCAT GGAAAGATTG TGAGAATTGT       420
TGATGTAGAG AAGGTTGAGA AAAGTTTCT CGGCAAGCCT ATTACCGTGT GGAAACTTTA       480
TTTGGAACAT CCCCAAGATG TTCCCACTAT TAGAGAAAAA GTTAGAGAAC ATCCAGCAGT      540
TGTGGACATC TTCGAATACG ATATTCCATT TGCAAAGAGA TACCTCATCG ACAAAGGCCT     600
AATACCAATG GAGGGGAAG AAGAGCTAAA GATTCTTGCC TTCGATATAG AAACCCTCTA       660
TCACGAAGGA GAAGAGTTTG GAAAAGGCCC AATTATAATG ATTAGTTATG CAGATGAAAA      720
TGAAGCAAAG GTGATTACTT GGAAAAACAT AGATCTTCCA TACGTTGAGG TTGTATCAAG      780
CGAGAGAGAG ATGATAAAGA GATTTCTCAG GATTATCAGG AGAAGGATC CTGACATTAT       840
AGTTACTTAT AATGGAGACT CATTCGACTT CCCATATTTA GCGAAAGGG CAGAAAAACT       900
TGGGATTAAA TTAACCATTG GAAGAGATGG AAGCGAGCCC AAGATGCAGA GAATAGGCGA     960
TATGACGGCT GTAGAAGTCA AGGGAAGAAT ACATTTCGAC TTGTATCATG TAATAACAAG    1020
GACAATAAAT CTCCCAACAT ACACACTAGA GGCTGTATAT GAAGCAATTT TTGGAAAGCC    1080
AAAGGAGAAG GTATACGCCG ACGAGATAGC AAAAGCCTGG GAAAGTGGAG AGAACCTTGA   1140
GAGAGTTGCC AAATACTCGA TGGAAGATGC AAAGGCAACT TATGAACTCG GAAAGAATT    1200
CCTTCCAATG GAAATTCAGC TTTCAAGATT AGTTGGACAA CCTTTATGGG ATGTTTCAAG    1260
GTCAAGCACA GGGAACCTTG TAGAGTGGTT CTTACTTAGG AAAGCCTACG AAAGAAACGA   1320
AGTAGCTCCA AACAAGCCAA GTGAAGAGGA GTATCAAAGA AGGCTCAGGG AGAGCTACAC   1380
AGGTGGATTC GTTAAAGAGC CAGAAAAGGG GTTGTGGGAA AACATAGTAT ACCTAGATTT   1440
TAGAGCCCTA TATCCCTCGA TTATAATTAC CCACAATGTT TCTCCCGATA CTCTAAATCT   1500
TGAGGGATGC AAGAACTATG ATATCGCTCC TCAAGTAGGC CACAAGTTCT GCAAGGACAT   1560
```

| | | | | | |
|---|---|---|---|---|---|
| CCCTGGTTTT | ATACCAAGTC | TCTTGGGACA | TTTGTTAGAG | GAAAGACAAA | AGATTAAGAC | 1620 |
| AAAAATGAAG | GAAACTCAAG | ATCCTATAGA | AAAAATACTC | CTTGACTATA | GACAAAAGC | 1680 |
| GATAAAACTC | TTAGCAAATT | CTTTCTACGG | ATATTATGGC | TATGCAAAAG | CAAGATGGTA | 1740 |
| CTGTAAGGAG | TGTGCTGAGA | GCGTTACTGC | CTGGGGAAGA | AAGTACATCG | AGTTAGTATG | 1800 |
| GAAGGAGCTC | GAAGAAAAGT | TTGGATTTAA | AGTCCTCTAC | ATTGACACTG | ATGGTCTCTA | 1860 |
| TGCAACTATC | CCAGGAGGAG | AAAGTGAGGA | AATAAAGAAA | AAGGCTCTAG | AATTTGTAAA | 1920 |
| ATACATAAAT | TCAAAGCTCC | CTGGACTGCT | AGAGCTTGAA | TATGAAGGGT | TTTATAAGAG | 1980 |
| GGGATTCTTC | GTTACGAAGA | AGAGGTATGC | AGTAATAGAT | GAAGAAGGAA | AAGTCATTAC | 2040 |
| TCGTGGTTTA | GAGATAGTTA | GGAGAGATTG | GAGTGAAATT | GCAAAGAAA | CTCAAGCTAG | 2100 |
| AGTTTTGGAG | ACAATACTAA | AACACGGAGA | TGTTGAAGAA | GCTGTGAGAA | TAGTAAAAGA | 2160 |
| AGTAATACAA | AAGCTTGCCA | ATTATGAAAT | TCCACCAGAG | AAGCTCGCAA | TATATGAGCA | 2220 |
| GATAACAAGA | CCATTACATG | AGTATAAGGC | GATAGGTCCT | CACGTAGCTG | TTGCAAAGAA | 2280 |
| ACTAGCTGCT | AAAGGAGTTA | AATAAAGCC | AGGAATGGTA | ATTGGATACA | TAGTACTTAG | 2340 |
| AGGCGATGGT | CCAATTAGCA | ATAGGGCAAT | TCTAGCTGAG | GAATACGATC | CCAAAAAGCA | 2400 |
| CAAGTATGAC | GCAGAATATT | ACATTGAGAA | CCAGGTTCTT | CCAGCGGTAC | TTAGGATATT | 2460 |
| GGAGGGATTT | GGATACAGAA | AGGAAGACCT | CAGATACCAA | AAGACAAGAC | AAGTCGGCCT | 2520 |
| AACTTCCTGG | CTTAACATTA | AAAAATCCTA | GAAAAGCGAT | AGATATCAAC | TTTTATTCTT | 2580 |
| TCTAACCTTT | TTCTATGAAA | GAAGAACTGA | GCAGGAATTA | CCAGTTCTTC | CGTTATTTTA | 2640 |
| TGGGTAATTA | AAAACCCATG | CTCTTGGGAG | AATCTTCGAA | TAAAATCCCT | AACTTCAGGC | 2700 |
| TTTGCTAAGT | GAATAGAATA | AACAACATCA | CTCACTTCAA | ACGCCTTCGT | TAGAAATGGT | 2760 |
| CTATCTGCAT | GCTTCTCTGG | CTCGGAANNG | GAGGATTCAT | AACAACAGTA | TCAACATTCT | 2820 |
| CAGAGAATTG | AGAAACATCA | GAAACTTTGA | CTTCTACAAC | ATTTCTAACT | TTGCAACTCT | 2880 |
| TCAAGATTTT | CTAAAAGAAT | TTTAACGGCC | TCCTCGTCAA | TTTCGACGAC | GTAGATCTTT | 2940 |
| TTTGCTCCAA | GCAGAGCCGC | TCCAATGGAT | AACACCCCTG | TTCCCGCACC | CAAGTCCGCT | 3000 |
| ACAATTTTTT | CCTTGTATCT | CCTAATGTAT | AAGCAAGCCA | AAGGAGAGTA | GATGCTACCT | 3060 |
| TTCCGGGAGT | TTTGTATTGC | TCTAGCCAAG | GTTTGGGATT | TTTGAATCCT | TTAACTCTGG | 3120 |
| AAAGTATAAT | TTCAAGCTCC | TTCTTCTTCA | TGACAGATGA | AAAATTGTTT | TGTCTCTTTT | 3180 |
| TAACTTTTAC | AGAAATAACT | GTCTCAAATT | ATGACAACTC | TTGACATTTT | TACTTCATTA | 3240 |
| CCAGGGTAAT | GTTTTAAGT | ATGAAATTTT | TCTTTCATAG | AGGAGGNNNN | NNGTCCTCTC | 3300 |
| CTCGATTTCC | TTGGTTGTGC | TCCATATGAT | AAGCTTCCAA | AGTGGGTGTT | CAGACTTTA | 3360 |
| GACACTCAAA | TACCAGACGA | CAATGGTGTG | CTCACTCAAG | CCCCATATGG | GTTGAGAAAA | 3420 |
| GTAGAAGCGG | CACTACTCAG | ATGCTTCCCC | AGGAATGAGG | TTGTTGTAGC | TCNTCCCNGA | 3480 |
| AAGATTGAGA | TGTTCTTGG | | | | | 3499 |

( 2 ) INFORMATION FOR SEQ ID NO:3:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO

-continued (iv) ANTI-SENSE: NO (xi) SEQUENCE DESCRIPTION: SEQ ID NO:3:

CTTGCCTTCG CTATAGCAAC CCTCTAT 27

(2) INFORMATION FOR SEQ ID NO:4:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:4:

GTAAAACGAC GGCCAGT 17